United States Patent [19]

Mullen et al.

[11] Patent Number: 5,358,866
[45] Date of Patent: Oct. 25, 1994

[54] CYTOSINE DEAMINASE NEGATIVE SELECTION SYSTEM FOR GENE TRANSFER TECHNIQUES AND THERAPIES

[75] Inventors: Craig A. Mullen, Bethesda; R. Michael Blaese, Rockville, both of Md.

[73] Assignee: The United States of America as represented by the Department of Health and Human Services, Washington, D.C.

[21] Appl. No.: 725,076

[22] Filed: Jul. 3, 1991

[51] Int. Cl.⁵ ............... C12P 21/06; C12N 5/00; C12N 9/78; C07H 21/04
[52] U.S. Cl. ............... 435/240.2; 435/69.1; 435/70.1; 435/227; 435/240.1; 435/252.3; 435/320.1; 536/22.1; 536/23.1; 536/23.2; 536/23.7; 536/23.74
[58] Field of Search ............... 435/69.1, 70.1, 227, 435/240.2, 240.1, 252.3, 320.1; 536/22.1, 23.1, 23.2, 23.7, 23.74

[56] References Cited

U.S. PATENT DOCUMENTS 4,975,278 12/1990 Senter et al. ............... 424/94.3

OTHER PUBLICATIONS

Bostrom et al. "Apolipoprotein B mRNA Editing" JBC 265(36) pp. 22446–22452 Dec. 25, 1990.

Breitman, M., et al.; "Genetic Ablation: Targeted Expression of a Toxin Gene Causes Microphthalmia in Transgenic Mice", Science, vol. 238, Dec. 11, 1987, pp. 1563–1565.

Nishiyama, T., et al.; "Neoplastic Effects in Rats of 5–Fluorocytosine in Combination with Cytosine Deaminase Capsules", Cancer Research, vol. 45, Apr. 1985, pp. 1753–1761.

Andersen, L., et al., Pryrimidine, Purine and Nitrogen Control of Cytosine Deaminase Synthesis In Escherichia coli K12 . . . , Arch Microbiol (1989) vol. 152, pp. 115–118.

Bennett, J. E., Goodman and Gilman's: The Pharmacological Basis of Therapeutics, 8th Edition, (Pergamon Press New York) pp. 1165–1181.

Eglitis, M. A., et al., Gene Expression in Mice After High Efficiency Retroviral–Mediated Gene Transfer, Science (1985) vol. 230, pp. 1395–1398.

Eglitis, M. A., et al., Retroviral Vectors for Introduction of Genes Into Mammalian Cells, BioTechniques, (1988) vol. 6, pp. 608–614.

Moolten, F. L., et al., Curability of Tumors Bearing Herpes Thymidine Kinase Genes Transferred By Retroviral Vectors, J. Natl. Cancer Institute (1990) vol. 82, pp. 297–300.

Borrelli, E., et al., Targeting of an Inducible Toxic Phenotype in Animal Cell, Proc. Natl. Acad. Sci. USA (1988) vol. 85, pp. 7572–7576.

Miller, A. D., et al., Improved Retroviral Vectors for Gene Transfer and Epression, BioTechniques (1989) vol. 7, pp. 980–990.

*Primary Examiner*—Robert A. Wax
*Assistant Examiner*—Hyosuk Kim
*Attorney, Agent, or Firm*—Townsend and Townsend Khourie and Crew

[57] ABSTRACT

The present invention relates to a system comprising a modified bacterial gene for cytosine deaminase that has been engineered into a eukaryotic expression vector and the expression of the gene by mammalian cells.

The present invention further relates to methods, gene therapies and vaccines that employ the negative selectable marker, cytosine deaminase, which has the ability to produce a toxic antimetabolite 5-fluorouracil from 5-fluorocytosine.

6 Claims, 2 Drawing Sheets

CYTOSINE DEAMINASE NEGATIVE SELECTION SYSTEM FOR GENE TRANSFER TECHNIQUES AND THERAPIES

BACKGROUND OF THE INVENTION

1. Field of the Invention

The present invention relates to a system comprising a modified bacterial gene for cytosine deaminase that has been engineered into a eukaryotic expression vector and the expression of the gene by mammalian cells.

The present invention further relates to methods, gene therapies and vaccines that employ the negative selectable marker, cytosine deaminase, which has the ability to produce a toxic antimetabolite 5-fluorouracil from 5-fluorocytosine.

2. Background Information

Selectable genetic markers are important tools in the study of the regulation and function of genes and are potentially important in gene transfer therapies. Conferring unique resistance or sensitivity to cytotoxic agents enables the skilled artisan the ability to select or delete genetically altered cells from a mixed population.

The enzyme cytosine deaminase (CD) is useful in the present invention as a selectable genetic marker because of its ability to catalyze the deamination of cytosine to uracil (M. Kilstrup et al., *J. Bacteriology* 171:2124–2127 (1989); L. Anderson et al., *Arch. Microbiol.* 152:115–118 (1989)). Bacteria and fungi which express this gene convert 5-fluorocytosine (5FC) to 5-fluorouracil (5FU) and this metabolite is toxic to the microorganism (A. Polak and H. J. Scholer, *Chemotherapy (Basel)* 21:113–130 (1975)). Mammalian cells do not express significant amounts of cytosine deaminase and do not deaminate 5FC (A. Polak et al., *Chemotherapy* 22:137–153 (1976); B. A. Koechlin et al., *Biochemical Pharmacology* 15:434–446 (1966)); 5FC is relatively nontoxic to them (J. E. Bennett, in Goodman and Gilman: the Pharmacological Basis of Therapeutics. 8th ed., eds. A. G. Gilman, T. Rall, A. S. Nies and P. Taylor (Pergamon Press, New York) pp. 1165–1181). However, 5FU has potent cytotoxic effects on mammalian cells. 5FU is subsequently metabolized to FUTP and FdUMP and thereby inhibits both RNA and DNA synthesis and kills the cell (P. Calabrisi and B. A. Chabner in Goodman and Gilman: the Pharmacological Basis of Therapeutics. 8th ed., eds. A. G. Gilman, T. Rall, A. S. Nies and P. Taylor (Pergamon Press, New York) pp. 1209–1263); L. E. Damon et al., *Pharmac. Ther.* 43:155–189 (1989)). Thus, intracellular metabolic conversion of 5FC to 5FU should be lethal to mammalian cells.

The bacterial gene for cytosine deaminase has recently been isolated and cloned (L. Anderson et al., (1989)). The present invention provides a new negative selectable marker in which the gene for cytosine deaminase from a microorganism, of which bacteria is an example, is modified and integrated into a eukaryotic expression vector and expressed in mammalian cells conferring upon the transfected cells a unique susceptibility to the cytotoxic effects of 5FC. The present invention also provides methods that use the cytosine deaminase negative selection system in vitro to selectively eliminate subpopulations of cells, and in vivo for gene transfer therapies and vaccines.

SUMMARY OF THE INVENTION

It is an object of the present invention to provide a novel expression gene construct containing a modified cytosine deaminase (CD) gene in mammalian cells and subsequent sensitivity of the mammalian cells engineered with the modified CD gene to 5-fluorocytosine (5FC).

Another object of the present invention is to provide methods that require the application of the CD gene construct or modifications of it in a variety of therapeutics including immunotherapy, gene therapy and bone marrow transplantation.

Various other objects and advantages of the present invention will become obvious from the drawings and the detailed description of the invention.

In one embodiment, the present invention relates to a DNA construct that comprises a modified cytosine deaminase gene from a microorganism and a eukaryotic expression vector. Examples of microorganisms are bacteria and fungi.

In another embodiment, the present invention relates to the DNA plasmid construct designated pCD2 which has the accession #40999.

In a further embodiment, the present invention relates to a mammalian host cell comprising the DNA construct of the modified cytosine deaminase gene and a eukaryotic expression vector. In a further aspect of the invention, mammalian host cells comprising the modified bacterial cytosine deaminase DNA construct expresses cytosine deaminase protein.

In another embodiment, the present invention relates to a CD negative selection marker system that provides a safety system in gene transfer therapies comprising the steps of inserting the DNA construct comprising a modified CD gene, eukaryotic expression, and exogenous DNA into a host or patient genome and treating the host or patient cells with 5FC in pharmacologically acceptable doses that will selectively kill cells that have integrated the DNA construct into their genome.

In another embodiment, the present invention relates to a method of gene therapy that regulates the gene product expression in a host comprising the steps of inserting a DNA construct comprising a modified CD gene, eukaryotic expression vector, and a therapeutic gene of interest into a host cell resulting in altering the host cell and treating the altered host cell with periodic doses of 5FC in pharmaceutical amounts such that the numbers of the host cell is diminished but not completely destroyed. In a variation of the method of regulating gene product expression in a host the methods described above is modified such that treatment with 5FC is in higher doses such that all the altered cells are destroyed.

The present invention further relates to live tumor vaccines for mammals comprising the modified CD gene and eukaryotic expression vector and tumor cells.

In another aspect, the present invention provides a method for treating tumors in a patient comprising the administration of acceptable doses of live the vaccine described above to a patient and subsequently administering a high dose of 5FC that will destroy the live cells used as vaccine.

In a further embodiment, the present invention relates to a vaccine for mammals against a microbiologic pathogen comprising a live unattenuated virus, bacteria or protozoa, a modified CD gene and expression vector in amounts sufficient lo to induce immunization against the virus, bacteria or protozoan.

In a further embodiment, the present invention relates to a method of vaccination against a microbiological pathogen comprising administering the vaccine described above to a host and subsequently administering a high dose of 5FC sufficient enough to destroy the live immunogen.

In a further embodiment, the present invention relates to a method of administering an allogeneic or autologous bone marrow transplant into a patient comprising the steps of treating the bone marrow transplant with a modified CD construct packaged into a vector in such a matter that the construct will preferentially infect tumor cells or lymphocytes but not bone marrow stem cells and subsequently treating the bone marrow cells with 5FC in doses such that the tumor cells or lymphocytes are completely purged or destroyed and administering the treated bone marrow cells in patient. In a modification of the above technique, the 5FC treatment may be given subsequent to the administration of the bone marrow transplant in a patient.

In yet another embodiment, the present invention relates to a double negative selection vector comprising the modified CD gene, and the herpes thymidine kinase gene in a eukaryotic expression vector.

In yet another embodiment, the present invention relates to a diagnostic method for detecting successful homologous recombination events comprising the steps of inserting a modified CD DNA construct into a cell line in vitro, creating a deletion mutant that will retain significant homology in a DNA sequence of the CD DNA construct but render the CD gene biologically inactive and detecting successful homologous recombination by measuring the loss of sensitivity to 5FC.

In another embodiment, the present invention relates to a method for selectively eliminating tissues in an animal comprising the steps of inserting a modified CD DNA construct comprising a modified CD gene and a tissue specific promoter into an animal cell and subsequently treating the animal with 5FC to eliminate the tissue corresponding to the tissue specific promoter.

In yet another embodiment, the present invention relates to a method of cancer therapy in a patient comprising the steps of administering to a patient a therapeutic dose of a DNA construct comprising a modified CD gene and a promoter with a predilection for transducing cancer cells and subsequently treating the patient with a toxic dose of 5FC that will destroy the cancer cells but not other cells.

The entire contents of all publications mentioned herein are hereby incorporated by reference.

Figure 1:
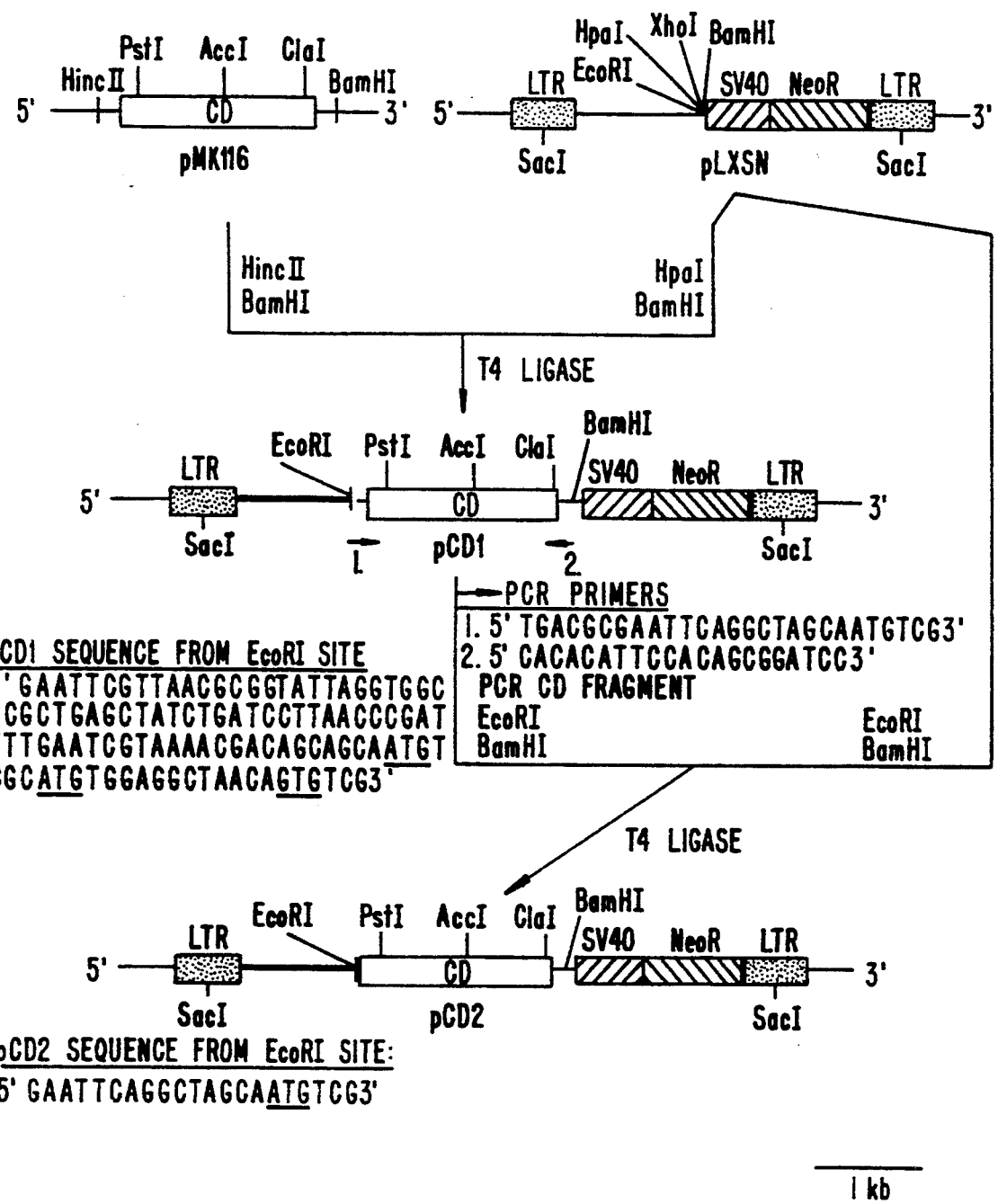
FIG. 1 shows the construction of pCD2. Cloning of the cytosine deaminase gene into eukaryotic expression vector pLXSN was performed in the following way. The 1.7 kb cytosine deaminase fragment from pMK116 digested by HincII and BamHI was ligated into the polycloning site of pLXSN digested with HpaI and BamHI, producing pCD1. The sequence of pCD1 in the 5' region at the EcoRI site near the start site GTG is shown. Oligonucleotide directed mutagenesis of pCD1 and recloning of the modified cytosine deaminase gene into pLXSN to produce pCD2 were subsequently undertaken. PCR primers (FIG. 1) and pMK116 (L. Anderson et al., (1989)) were used to eliminate upstream ATG's and change GTG to ATG at the start codon. The modified cytosine deaminase gene was then cloned into pLXSN. The sequence of pCD2 in the 5'region of the start codon beginning at the EcoRI site near is shown.

Panel A represents the Southern analysis on PCR products using cellular DNA as template for cytosine deaminase DNA synthesis. 1 μg cellular DNA underwent PCR using primers corresponding to the 5' and 3' ends of the modified cytosine deaminase gene. PCR product was electrophoresed, blotted by capillary transfer and probed with a 32P-labelled cytosine deaminase probe. The bands seen correspond to a 1.7 kb fragment.

Panel B represent the Southern analysis of cellular DNA. 10 μg cellular DNA was digested with SacI, electrophoresed, transferred and probed with the same probe. SacI cuts through both LTR elements of pCD2 and should generate from unrearranged DNA a 4.5 kb fragment containing the cytosine deaminase sequence. As a positive control 1 μg 3T3 DNA was supplemented with 30 pg pCD2 (3T3+pCD2) prior to digestion with Sac I.

DETAILED DESCRIPTION OF THE INVENTION

The present invention relates, in part, to the insertion of the a cytosine deaminase (CD) gene derived from a microorganism into a eukaryotic expression vector. A principle embodiment of this aspect of the present invention relates to the successful expression of the CD gene in mammalian cells and the subsequent sensitivity of cells expressing the gene to the toxic effect of 5-fluorocytosine, an agent nontoxic to unaltered mammalian cells. The present invention also relates to methods that apply to the above CD gene selectable marker in gene transfer studies and therapies.

The cytosine deaminase (CD) gene underwent modification in and around the start site for eukaryotic expression. Without these modifications the cytosine deaminase was poorly expressed in mammalian cells even when cloned into a strong expression vector like pLXSN. In particular, the present invention relates to the constructed bacterial gene for CD in an eukaryotic expression vector, for example, pCD2 and the expression of the gene in mammalian cells, for example, murine fibroblasts.

The cytosine deaminase gene is found and expressed in a variety of microorganisms. Examples include the fungi *Cryptococcus neoformans, Candida albicans, Torulopsis glabrata, Sporothrix schenckii,* Aspergillus, Cladosporium, and Phialophora (J. E. Bennett, Chapter 50: Antifungal Agents, in Goodman and Gilman's *the Pharmacological Basis of Therapeutics* 8th ed., A. G. Gilman, ed., Pergamon Press, New York, 1990) and the bacteria *Escherichia coli* and *Salmonella typhimurium* (L. Andersen, et al., *Archives of Microbiology*, 152; 115-118, 1989 ). In these microorganisms the genetically encoded enzyme serves the same purpose: to help provide uracil from cytosine for nucleic acid synthesis. The *E. coli* enzyme and gene are representative of the group.

The distinguishing feature of the present invention is the expression of the CD gene in higher eukaryotic cells for the purpose of creating a negative selection system. One skilled in the art of molecular biology may express the modified CD gene in a variety of other eukaryotic expression vectors to achieve the same purposes as those disclosed herein.

Introduction of the gene into mammalian cells results in the ability of transfected cells to convert cytosine to uracil; normally mammalian cells do not contain the enzyme cytosine deaminase. In vitro conversion of radiolabelled cytosine to uracil is consistently seen with transfected cells. The presence and expression of the gene has no apparent deleterious effects upon the cells if they are not exposed to 5FC. However, when such cells were exposed to 5FC they cease proliferation and die as judged by their failure to produce colonies in clonogenic assays and impaired proliferation in $^3$H-thymidine uptake assays (See Example 3). The toxicity was due to the deamination of 5FC to 5FU by the cells. Normal cells were not inhibited by 5FC and only those cell lines with demonstrable cytosine deaminase activity in vitro were sensitive to 5FC toxicity.

The ability to render cells selectively susceptible to the toxic effects of 5FC is important in implementing the present invention of the CD negative selection system in a variety of therapeutic assays and vaccines described below.

The present invention describes the novel expression of the modified cytosine deaminase gene in mammalian cells and subsequent sensitivity of cells engineered with the modified CD gene to 5FC. The inventions described below involve either direct application of the plasmid pCD2 or modifications of it that would be easily performed by an individual skilled in the art of molecular biology given the information applicants have provided about the cytosine deaminase negative selection system and knowledge and materials regarding other eukaryotic gene expression promoters/enhancers and retroviral packaging cell lines that are in the public domain.

The present invention is the first to demonstrate that the bacterial enzyme for cytosine deaminase when appropriately modified in sequence and placed under control of a eukaryotic promoter can be inserted into the genome by transfection or retroviral transduction and render cells selectively sensitive to 5FC. By providing the present invention of rendering mammalian cells sensitive to 5FC through engineering of the cytosine deaminase gene, one skilled in the art will be enabled to apply the cytosine deaminase negative selection system (CDNSS) to a variety of tissues by simply applying known techniques in molecular biology and retrovirology. Multiple tissue-specific promoter/enhancer sequences have been described. As representative examples of these promoter/enhancer elements the following references are listed: *Muscle and neural:* E. Barnea et al. *Neuron* 5:881–888 (1990); *Thyroid:* C. Ledent et al., *Proc. Natl. Acad. Sci. USA* 87: 6176–6180 (1990); *Lymphoid:* G. P. Cook & M. S. Neuberger, *Nucleic Acids Res.* 18:3665–3671 (1990); *hepatic* P. Herbomel et al., *Mol. Biol.* 9:4750–4758 (1989) and M. G. Izban et al., *J. Biol. Chem.* 264:9171–9199 (1989); Bone Marrow: J. Magram et al., *Mol. Cell Biol.* 9:4750–4758 (1989).

Using cloning techniques described herein and elsewhere a tissue-specific promoter/enhancer could be inserted in pCD2 resulting in activation of the cytosine deaminase gene in a specific tissue. One example of this would be use of the immunoglobulin heavy chain promoter/enhancer to activate the gene in B-cells (S. Eccles et al. *New Biol.* 2:801–811 (1990); J. Wang et al. *Mol. Cell Biol.* 11:75–83 (1991); B. Porton et al. *Mol. Cell Biol.* 10:1076–83 (1990); C. Queen & D. Baltimore, *Cell* 33:717–728 (1983); E. E. Max. "Immunoglobulins: molecular Genetics" in W. E. Paul (ed.) *Fundamental Immunology* (2nd. ed.) Raven Press, New York, pp.235–290 (1989)).

Another way to confer tissue specificity may be to deliver the CDNSS using the pCD2 plasmid in different packaging cell lines, an example of which is the cell line PA317 we describe here. A variety of retrovirus packaging lines which have different cell-type and species tropisms have been described (A. D. Miller *Human Gene Therapy* 1:5–14 (1990)). One skilled in the art of molecular biology would have no difficulty taking the invention and transfecting it by calcium phosphate precipitation into a different packaging cell line which would then change the target cell specificity of the CDNSS.

In one embodiment, the present invention relates to a CD negative selection marker system that may provide a safety system in gene transfer therapies. Because gene therapy involves insertion of exogenous DNA into a host's or patient's genome, it is possible that malignant transformation of the target cells will result. The CD system may be used to destroy the malignant cells.

This application could be achieved in several ways given the present invention described herein about the cytosine deaminase negative selection system (CDNSS). First, target cells for gene therapy could first be treated with CDNSS and only cells that have incorporated the sequence as judged by neomycin resistance could then be subject to gene therapy with a second vector carrying a therapeutic gene. This two-step process would ensure that any cells altered by the therapeutic gene vector would also have the CDNSS present.

Second, the CDNSS could be modified by someone skilled in the art of molecular biology to incorporate the CDNSS and the therapeutic gene in the same vector. The number of ways of accomplishing this is great. One example would be to clone a therapeutic gene and a promoter element into pCD2, either replacing the neomycin resistance gene or by adding a third gene to pCD2. Another example would be excision with restriction endonucleases of the unique element of the CDNSS, the modified cytosine deaminase gene, and its cloning into another plasmid or retrovirus that harbors the therapeutic gene. Any cell altered by the vector would then contain the CD gene. If that cell or its progeny became malignant, the patient or host could be treated with 5FC (5-fluorocytosine) and the cells would be killed.

Similarly, the CD gene could be used to destroy cells altered by gene therapy if they produced a substance that was toxic to the patient. For example, if tumor necrosis factor was to be used in gene therapy, the CDNSS of modified cytosine deaminase gene could be included in the vector. Then if the transferred cells made amounts of TNF that were toxic to the host, the patient could receive 5FC. The transferred cells would be destroyed and the TNF production would cease. This approach may be used with any therapeutic gene that may have unforeseen or unacceptable side-effects.

The present invention further relates to a method for controlling the gene expression in gene therapy by applying the CD negative selection system. The CD system of the present invention may be used to regulate the amount of gene product the host or patient receives.

The CDNSS could be used to regulate gene dosage in a manner similar to that described above in the discussion of controlling malignant cells or cells that were produing unacceptable side-effects. That is, target cells could first be engineered with the unmodified CDNSS and only cells that had first been modified with it could then be subjected to a second manipulation with a vector containing a therapuetic gene. Or an individual skilled in the art of molecular biology could move the essential element of the CDNSS, the modified CD gene, into another vector that harbored the therapeutic gene and use a single vector to transfer the CDNSS and the therapeutic gene. An example of the application follows. For example, a gene for erythropoietin and CD may be cloned into the same vector used in gene therapy to treat anemia. After infusion of many vector containing cells, a high serum level of hormone may be achieved. Low doses of 5FC could be given periodically to the patient to diminish in size the pool of cells producing hormone and thus reduce the serum level of the hormone to the level desired. Similarly, if one wished to expose a patient to gene therapy for only short periods of time instead of permanently keeping gene altered cells in the patient, high doses of 5FC could be given to the patient at the end of the prescribed period and destroy all the producing cells. This method may be used with any therapeutic gene, for example, insulin, growth hormone, clotting factors or growth factor.

The present invention further relates to live tumor vaccines containing the CD gene. Immunotherapy of malignancy may involve using a vaccine of a host's tumor extracts or cells to enhance the host's immune response to the tumor (B. Gansbacher et al., *J. Exp. Med.* 172:1217-1224 (1990)). Live vaccines are more effective than killed cells or cell extracts as has been shown by vaccine development in the areas of virology and bacteriology. However, administering live tumor as vaccine to patients is dangerous because the early immune response to it may not complete destroy it; the tumor still would have the potential to invade locally and metastasize. However, introducing the CDNSS into live tumor cells by transfection, by retroviral transduction or other gene transfer techniques using the same methods used with 3T3 or PA317 cells would then make the tumor sensitive to 5FC. This may allow safe use of a live tumor vaccine. For example, two weeks after inoculation of tumor the patient or host could receive 5FC. This would destroy the tumor inoculum but leave the immune cells of the host undamaged.

The present invention further relates to novel live vaccines and novel methods for producing "attenuated" or controllable pathogens as immunogens. Some viruses, bacteria and protozoa are quite virulent and cannot be used in immunization. Traditional methods of developing attenuated strain can result in organisms that are not optimally immunogenic. The CD system of the present invention may be used to produce a controllable pathogen for immunization. The unique feature of the CDNSS in this context is its ability to destroy with 5FC cells that harbor intracellular pathogens. Using the techniques described herein to clone the modified cytosine deaminase sequence gene into pLXSN, the CDNSS could be modified to contain the cytosine deaminase gene and elements of other viruses. For example, elements of the HIV genome (the agent responsible for AIDS and for which techniques of live virus immunization are currently unsafe) could be cloned into the CDNSS. The modified gene expression system would express cytosine deaminase and HIV. The modified CDNSS could then be given to patients and after the innoculation had initiated an immune response to the HIV elements 5FC could be administered to and inhibit further transcription and translation of the HIV elements. This would be analogous to treatment of herpes simplex infections with acyclovir or ganciclovir (R. G. Douglas, "Antiviral Agents" In A. G. Gilman (ed) *Goodman and Gilman's the Pharmacological Basis of Therapeutics* (8th ed), pp. 1184-1887 (1990)).

In yet another embodiment, the present invention relates to a method of therapy of human immunodeficiency virus (HIV) infection using the CD negative selection system. As noted in other parts of this application, the CDNSS could be altered by someone skilled in the art of molecular biology in a variety of ways. One alteration would be the replacement of the promotor driving expression of the cytosine deaminase gene with another promotor. Promotor/enhancer elements from the HIV genome responsive to HIV transactivation could be inserted upstream of the cytosine deaminase gene (K. A. Jones *New Biol.* 1:127-135 (1989)). Intracellular HIV activity would then result in activation of the cytosine deaminase gene. This would provide a novel therapy for HIV infection. White blood cells from an HIV positive individual could be removed by standard leukapheresis, infected in vitro with the CDNSS and returned to the patient who would then receive 5FC. Cells that contained HIV would then activate the CDNSS via transactivation and be eliminated by 5FC. The propagation of the HIV infection would thus be curtailed in the patient.

In another embodiment, the present invention relates to a therapeutic method for use in allogeneic or autologous bone marrow transplantation. It is often desirable in bone marrow transplantation to eliminate certain cells from the bone marrow before they are infused into a patient. For example, one may want to purge residual tumor cells or eliminate certain cells that could cause graft-versus-host disease in the bone marrow recipient. The CD system of the present invention may be used in such purging strategies. For example, it could be packaged into a vector that will preferentially infect tumor cells but not the bone marrow stem cells. The tumor calls but not the stem cells will be sensitive to 5FC.

It has been documented that retroviral gene insertion will not occur in cells that are not replicating, i.e., those that remain in Go of the cell cycle (D. G. Miller, et al. *Mol. Cell Biol.* 9:1426-1434 (1990)). This phenomenon provides a basis for selective infection of tumor cells in bone marrow infiltrated with tumor. The bone marrow stem cells without specific hormonal stimulation in vitro remain quiescent while the tumor cells naturally cycle. Exposure of this infiltrated marrow to retrovirus carrying the CDNSS will then result in insertion of the CD gene into the tumor cells but not the quiescent bone marrow stem cells. Pretreatment of the bone marrow prior to infusion or administration of 5FC to the patient after bone marrow infusion will result in purging of the infected tumor cells. Similarly, the CD gene of the present invention may be packaged in a vector that will preferentially infect lymphocytes but not stem cells and 5FC used to purge the marrow of lymphocytes prior to infusion, or administered to the patient to prevent or treat graft-versus-host disease.

In a further embodiment, as a diagnostic assay, the CD system of the present invention may be used as a reporter marker for successful homologous recombination. Using methods identical to those described to insert the CDNSS system into the 3T3 or PA317 cells, one could stably integrate the CDNSS into a cell line in vitro. One skilled in the art of molecular biology could use the present invention regarding the restriction sites in the CDNSS to create a deletion mutant which would retain considerable homology to the DNA sequence of the CDNSS but would not yield biological active cytosine deaminase. This technique is commonly used in molecular biology. The deletion mutant and the CDNSS could then be used in homologous recombination trials with loss of sensitivity to 5FC as a marker for successful recombination. Such homologous recombination trials have been performed with other selectble markers or reporter genes in studies of targeted gene insertion (R. J. Bollaf, et al., *Annu. Rev. Genet.* 23:199–225 (1989)).

In another embodiment, the CD system of the present invention may be used in co-cultivation transduction methods with viral vectors.

A known technique in molecular biology and retroviral gene transfer studies is cocultivation in vitro of target cells and the retrovirus producer cell line. This results in intimate contact of target cells with supernatant whose retrovirus content is continuously being renewed (M. A. Eglitis, et al., *Science* 230:1395–1398 (1985); M. A. Eglitis & W. F. Anderson, *BioTechniques* 6:608–614 (1988)). In viral transduction techniques of gene transfer, cell-free vital supernatant is harvested from virus producer cell lines that produce virus. Target cells are then exposed to the supernatant. However, the vital supernatant is unstable at temperatures used for transduction and loses all its activity in a few hours. An alternate strategy is to mix in culture live virus producer lines and target cells. They can be cocultivated for a long time resulting in much more efficient transduction of the target cells. This is because the producer line is continuously making live virus. This cannot be done for gene therapy currently because it is very difficult to separate the producer and target cell lines and have only purified target cells to give to the patient. However, if the CD gene system of the present invention were transfected into the producer line in a form that would not result in packaging of the CD gene, the virus producer cells could be purged from the co-cultivation culture by adding 5FC to the medium after the desired period of virus exposure was complete. Then only the desired target cells would survive and may then be given to the host.

The present invention further relates to novel methods that create double negative selection vectors. The CD gene system of the present invention may be inserted along with the herpes thymidine kinase gene into a gene transfer vector along with other genes. Then the cells receiving the vector may be sensitive to both 5FC and ganciclovir or acyclovir, providing a double negative selection system for eliminating gene modified cells. This may be advantageous as some cells may not be eliminated with CD/5FC or TK/ganciclovir alone (F. L. Moolten & J. M. Wells, *Journal of the Natl. Cancer Inst.* 82:297–300 (1990)). In combination they may provide additive or possibly even synergistic toxicity.

The present invention also relates to methods for producing transgenic animals by incorporating the CD gene of the present invention into the germ-line of an animal. The CD gene system of the present invention may be inserted into the germ-line of an animal, for example, a mouse. The CD gene may be combined with a variety of tissue-specific promoters, which will result in CD being expressed only in those tissues in which the promoter is active, for example, in B-cells if an immunoglobulin promoter is used (E. Borrelli et al., *Proc. Natl. Acad. Sci. USA* 85:7572–7576 (1988)). The 5FC may be used to selectively eliminate these tissues. This will be of use in studies of organ and tissue development.

In a further embodiment, the present invention relates to a therapeutic method for the treatment of cancer. As currently configured the CDNSS of the present invention will have a predilection for transduction of cancerous tissues as opposed to normal, nonneoplastic tissue. As discussed above, it has been shown that replicating cells permit retrovirus mediated gene insertion but quiescent cells do not (A. D. Miller, 1990). A patient could then be treated in vivo with the CDNSS of the present invention in retrovirus form and the patient's cancerous cells would be preferentially tranduced and become sensitive to 5FC. One skilled in the art of molecular biology would be able to increase the tissue specificity of the CDNSS by taking the information provided by the present invention of the CDNSS regarding the ability to render cells selectively sensitive to 5FC and by inserting known tissue-specific promoters into the CDNSS using standard techniques in molecular biology. (See earlier discussion of tissue-specific promoters for references). For example, one could rearrange the elements of the CDNSS in the following way to make the CDNSS active in B lymphocytes which would be useful in the treatment of B-cell leukemias and lymphomas. Using standard cloning techniques such as those used in the construction of pCD2 one could move the neomycin phosphotransferase gene immediately 3' to the LTR promoter, insert the promote/enhancer for the immunoglobulin heavy chain gene 3' to the neomycin phosphotransferase gene and 5' to the modified cytosine deaminase gene, and then delete the SV40 promoter. As the immunoglobulin promoters are preferentially active in cells of the B-lymphocyte lineage (S. Eccles et al. *New Biol.* 2:801–811 (1990); J. Wang et al. *Mol. Cell Biol.* 11:75–83 (1991); B. Porton et al. *Mol. Cell Biol.* 10:1076–1083 (1990); C. Queen & D. Baltimore, *Cell* 33:717–728 (1983); E. E. Max "Immunoglobulins: Molecular Genetics": in W. E. Paul (ed.) *Fundamental Immunology* (2nd. ed) Raven Press, New York, pp. 235–290 (1989)), the rearranged CDNSS would be useful in treatment of B-cell leukemias and lymphomas. The specificity for the tumor cells would be twofold: retroviral preference for proliferating cells for gene transfer and activation of the gene in cells of B-lymphocyte lineage.

The invention is described in further detail in the following non-limiting examples.

EXAMPLES

The following materials and methods were used throughout the Examples.
Molecular Techniques The plasmid pMK116 contains a 1.7 kb fragment from *E. coli* which contains the coding region for cytosine deaminase in the polycloning site of the vector pTZ18U (D. A. Mead et al., *Protein Engineering* 1:67–74 (1986)). The plasmid pLXSN contains eukaryotic expression elements: (5') Moloney murine sarcoma virus LTR promoter, polycloning site, SV40 early promoter, neomycin phosphotransferase gene, and Moloney murine leukemia virus promoter (3') (A. D. Miller and G. J. Rosman, *BioTechniques* 7:980–990 (1989)). The neomycin phosphotransferase gene allows cells to survive in the presence of the protein synthesis inhibitor neomycin or its analogue G418 (F. Colbere-Garapin et al., *J. Mol. Biol.* 150:1–14 (1981)). These vectors and the subsequent constructs are depicted in FIG. 1. pMK116 was digested with the restriction enzymes HincII and BamHI. pLXSN was digested with HpaI and BamHI. The 1.7 kb fragment from pMK116 and the 5.7 kb fragment from pLXSN were separated and isolated by electrophoresis in a low-melting point agarose. The fragments were then ligated with T4 ligase and transformation competent E. coli were transformed with the product (K. Struhl, BioTechniques 3:452-453 (1985)). Minipreps of individual colonies of transformants were screened for insertion and proper orientation of the cytosine deaminase gene in pLXSN by restriction digest analysis. Large scale preparations of plasmids were produced by standard methods and the plasmids purified by cesium chloride gradient centrifugation or by Quiagen columns (J. Sambrook et al., Molecular Cloning: A laboratory manual. 2nd ed. (Cold Spring Harbor Laboratory Press, Cold Spring Harbor, N.Y. (1989)). pCD1 represented the insertion of the unmodified bacterial cytosine deaminase sequence into pLXSN.

Oligonucleotide Directed Mutagenesis of pCD1

Oligonucleotides were synthesized on an Applied Biosystems 381A DNA Synthesizer and purified by polyacrylamide gel electrophoresis (J. Sambrook et al., (1989)). Oligonucleotides 5'TGA CGC GAA TTC AGG CTA GCA ATG TCG 3' (SEQ. ID NO. 3) (corresponding to the 5' end of the cytosine deaminase sequence) and 5'CAC ACA TTC CAC AGC GGATCC3' (SEQ. ID NO. 4) (antisense to the 3' region flanking the gene) were used as primers and pCD1 was used as template in a polymerase chain reaction using a Perkin Elmer Cetus DNA thermal cycler. The resulting 1.7 kb fragment and pLXSN were digested with EcoRI and BamHI, electrophoretically isolated and ligated with T4 ligase. E. coli were transformed and plasmids screened as above. The resulting plasmid with the altered cytosine deaminase sequence is called pCD2. The 5' region of the gene was sequenced by the dideoxynucleotide chain termination method to verify the desired sequence (J. Sambrook et al., (1989)). The same PCR primers mentioned above were used to amplify cytosine deaminase sequences in 1 µg of purified genomic DNA from transfected cells; the PCR product underwent Southern analysis using standard techniques (J. Sambrook et al., (1989)) and a $^{32}$P-labelled probe corresponding to the 1.7 kb cytosine deaminase gene found between the EcoRI and BamHI sites in pCD2 (J. Sambrook et al., (1989)) Southern blots using the same probe were also performed on SacI digests of 10 µg samples of purified genomic DNA from cell lines.

Cellular Technique

Cells were grown in D10, i.e, DMEM supplemented with 10% vol. heat-inactivated fetal calf serum, 2 mM glutamine, 50 U/ml penicillin and 50 µg/ml streptomycin, and incubated at 37° and 5% $CO_2$. NIH-3T3 cells and PA317 cells are mouse fibroblast cell lines which have been previously described (A. D. Miller and C. Buttumore, Mol. Cell. Biol. 6:2895-2902 (1986)). PA317 has been derived from NIH-3T3 cells and contains a stably integrated replication incompetent retroviral genome; it functions as a retroviral packaging line when transfected with plasmids containing a sequence encoding a retrovirus with an intact packaging signal. Plasmids pLXSN, pCD1 and pCD2 contain retroviral LTR's and an intact packaging signal. Cells were transfected with purified plasmid DNA using a standard calcium phosphate precipitation method (J. Sambrook et al., (1989)). The procedure for vital transduction has been previously described (K. Cornetta and W. F. Anderson, J. Virol. Meth. 23:186-194 (1988)). 3T3 cells were grown in supernatant from packaging lines and protamine 5 µg/ml for 24 hours and then D10 medium was substituted. 72 hours after transfection or 48 hours after transduction G418 1 mg/ml was added to the medium and cells were selected in this medium for 7 days. Thereafter the cells were maintained in D10 medium only. Clonogenic assays were performed as follows. Cells were diluted to $10^4$/ml and 0.1 ml were placed into 4 cm flat-bottomed wells of a 6 well Costar tissue culture dish along with 5 ml of medium with 5FC and/or G418 at concentrations described in the examples below and tables. They were incubated for 5 days at which time the wells were stained with Geimsa stain and colonies of greater than 25 cells were examined and counted with the aid of a 40× microscope. Proliferation assays were performed as follows. $10^3$ cells were placed in flat bottomed wells of a 96 well places containing 0.2 ml medium with additives as described in the tables and text. At the time indicated the wells were pulsed with 25 µl 3H-thymidine in RPMI with an activity of 0.5 µCi/25 µl. They were harvested 4 hours later with an automated cell harvester and counted in a scintillation counter. 12 replicates of each condition were performed. Standard t-test statistical methods were employed (G. W. Shedecor and W. G. Cochran, Statistical Methods ed.7. Iowa State University press, Ames, Iowa pp. 89-98, 124-128 (1980)).

Enzyme Assay

In vitro assay for cytosine deaminase was performed using a modification of previously described methods (L. Anderson et al., (1989)). $1 \times 10^6$ cells were centrifuged in a microfuge, washed once in normal saline, centrifuged again and resuspended in 10 µl of 100 mM Tris pH 7.8, 1 mM EDTA and 1 mM dithiothreitol. They were then subjected to 5 cycles of rapid freezing and thawing. The material was centrifuged 5 min. in a tabletop microfuge. 10 µl of supernatant was combined with 10 µl 3H-cytosine (5mM cytosine in 100mM Tris pH 7.8 with an activity of 0.5 µCi per 10 µl) and incubated for 4 hours. 10 µl of sample and 10 µl of a marker solution containing unlabelled cytosine 0.4 mg/ml 10 and unlabelled uracil 0.4 mg/ml in water were placed on thin layer chromatography sheets (Kodak Chromatogram Sheet 13254) and developed in a mixture of 1-butanol (86%) and water (14%). After drying, spots corresponding to cytosine and uracil were cut out under short wave UV illumination and assayed in a scintillation counter. The radioactivity recovered from the cytosine and uracil bands accounted for essentially all the label introduced to the sample as judged by counting the activity of 10 µl of label not subjected to chromatographic separation.

EXAMPLE 1

Rationale for Gene Cloning

FIG. 1 summarizes the cloning process. Initially the entire unmodified coding region for cytosine deaminase from pMK116 was cloned into the polycloning site of pLXSN. The resulting construct was named pCD1. When transfected into 3T3 cells there was little evidence of gene expression, sequencing of the noncoding region immediately 5' of the coding region of the cytosine deaminase gene revealed the following sequence: 5' . . . CAATGTCGCATGTGGAGG-CTAACAGTGTCG . . . 3' (SEQ. ID NO. 5) (FIG. 1). Analysis of the protein in bacteria revealed that translation began at the GTG codon. As described in the material and method section above and outlined in FIG. 1, the 5' upstream sequence was altered using oligonucleotide directed mutagenesis and the gene was cloned into pLXSN under the LTR promoter upstream of the polycloning site. The resulting plasmid containing the engineered sequence is called pCD2. This construct has been deposited at the American Type Culture Collection in Rockville, Md. on Apr. 11, 1991 under the terms of the Budapest Treaty. The plasmid has been given the accession number of 40999. Sequencing of the 5' region of the cytosine deaminase gene verified the desired sequence and deletion of 88 base pairs upstream of the start site in pCD1, the unmodified plasmid containing the bacterial gene. FIG. 1 summarizes the salient sequences from pCD1 (the unmodified sequence) and pCD2. pCD2 contains the following eukaryotic expression elements: LTR promoter promoting the cytosine deaminase gene followed by the SV40 early promoter promoting the gene encoding neomycin phosphotransferase.

EXAMPLE 2

Figure 2A:
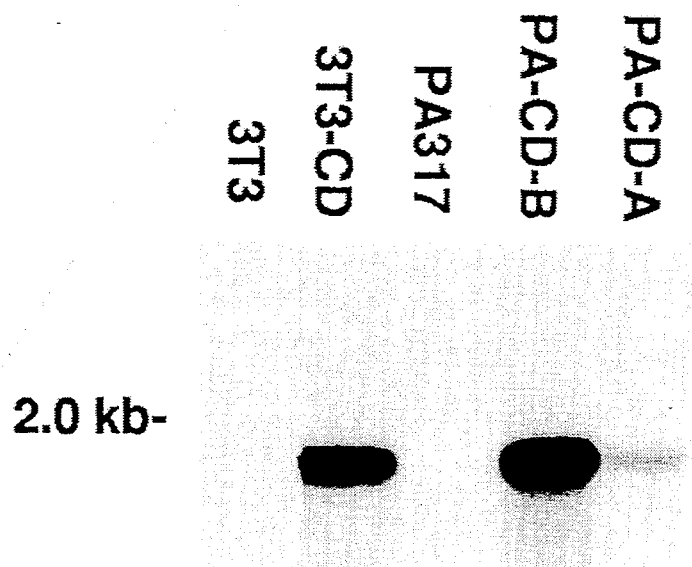
FIG. 2 is a Southern analysis detecting the presence of cytosine deaminase gene in genomic DNA of cells transfected with pCD2.
Figure 2B:
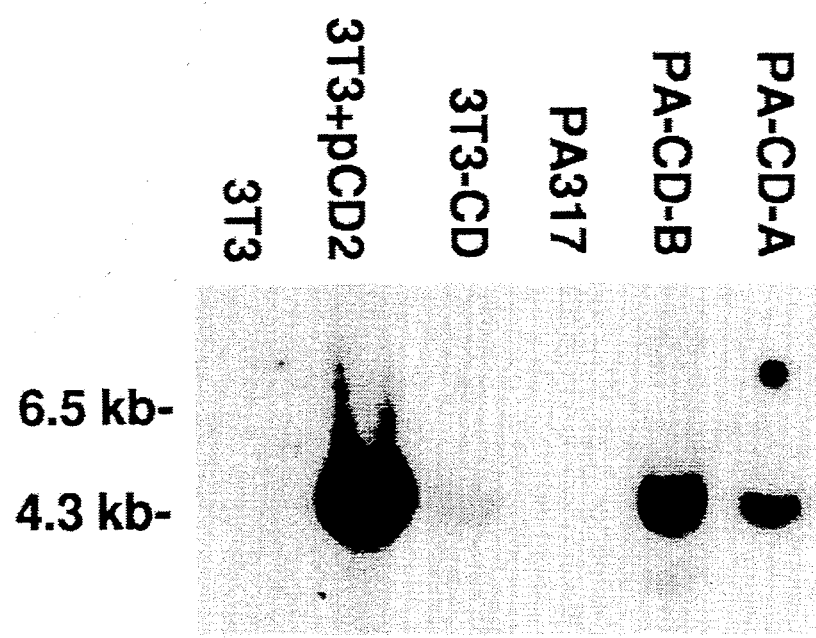

Transfection of Mammalian Cells With pCD2 Results in Expression of the Cytosine Deaminase Gene 3T3 and PA317 cells were transfected with pCD2 and 72 hours later were placed in medium containing G418 1 mg/ml. The cells were incubated in G418 for 7 days and then maintained in regular medium. Resistance to the neomycin analogue G418 allowed for enrichment of the population of cells with those that had taken up and incorporated plasmid sequences. Line 3T3-CD represents a transfection of 3T3; PA-CD-A and PA-CD-B represent separate transfections of PA317. Incorporation of the cytosine deaminase gene into the genome was demonstrated in two ways. First, PCR reactions employing primers corresponding to the 5' and 3' ends of the cytosine deaminase gene (see FIG. 1) were used to amplify the gene; Southern blot using a full length cytosine deaminase DNA probe demonstrated the 1.7 kb gene in 3T3-CD, PA-CD-A and PA-CD-B DNA but not in control 3T3 or PA317 (FIG. 2). Second, Southern analysis of genomic DNA digected with Sac I using the same probe demonstrated the gene (FIG. 2).

These cell populations was assayed for expression of the cytosine deaminase gene. An in vitro enzyme assay measured the conversion of radiolabelled cytosine to uracil by lysates of cells. Cell lines 3T3-CD, PA-CD-A and PA-CD-B demonstrated cytosine deaminase activity by converting cytosine to uracil while the nontransfected control lines did not (Table 1).

TABLE 1

Conversion of cytosine to uracil in vitro by lysates of cell lines containing the cytosine deaminase gene.

| Cell line lysate | Cytosine deaminase activity, Units[1] | | | |
|---|---|---|---|---|
| | Exp. 1 | Exp. 2 | Exp. 3 | Exp. 4 |
| Buffer only | 0.2 | 0.1 | 0.1 | 0.1 |
| 3T3 | 0.6 | 0.1 | 0.1 | 0.1 |
| 3T3-CD | 5.6 | 1.7 | 3.4 | — |
| PA317 | — | 0.1 | 0.1 | — |
| PA-CD-A | 13.3 | 17.0 | 15.7 | 17.1 |
| PA-CD-B | — | 18.3 | 16.1 | — |
| 3T3-CD-V1 | — | — | — | 17.5 |
| 3T3-CD-V2 | — | — | — | 16.4 |

[1]Values represent conversion of radiolabeled cytosine to iracil by cell lysates in vitro. 1 unit of cytosine deaminase activity is defined as 1U = 1 pmole uracil produced/$10^8$ cells/min.
(—) = not done.

EXAMPLE 3

Cell Lines Expressing the Cytosine Deaminase Gene are Sensitive to 5FC Toxicity

Clonogenic assays were performed to assess the sensitivity of cells to 5FC. $10^3$ cells were inoculated into 4 cm wells and after 5 days the number of colonies resulting from the inoculum were counted. Individual cells that can survive and proliferate in that environment can give rise to individual colonies. The inoculum was dilute enough to allow easy identification and enumeration of individual colonies. One would predict that cells expressing the cytosine deaminase gene could not give rise to colonies in the presence of 5FC as they would produce toxic 5FU. Similarly cells not expressing the neomycin resistance gene ought not to grow in the presence of G418.

Assuming a sequence containing both cytosine deaminase and neomycin resistance genes has been integrated into the cell's genome and that both genes are expressed, no cell which can survive in G418 should survive in 5FC and the relative cloning efficiency should drop to near zero. Table 2 demonstrates that this is indeed the case for those cell lines which express cytosine deaminase activity in vitro. For 3T3-CD, PA-CD-A and PA-CD-B, the colony counts in G418 were generally greater than two-thirds of those in medium only controls indicating considerable enrichment of the population with cells that had incorporated plasmid and expressed enough neomycin phosphotransferase to survive in G418 1 mg/ml. In 5FC alone the relative colony counts were 3–15% control counts indicating that the vast majority of the transfected cells were sensitive to 5FC. 5FC did not reduce the cloning efficiency of 3T3 or PA317 cells and thus the effect could not be attributed to the inherent toxicity of 5FC to mammalian cells. In medium containing both 5FC and G418 almost no colonies of the cytosine deaminase expressing lines were found.

TABLE 2

Relative cloning efficiency in G418 and/or 5FC of cell lines containing the cytosine deaminase gene.

| Cell line | Medium additive | Ave. colony number (sem) | |
|---|---|---|---|
| | | Exp. 1 | Exp. 2 |
| 3T3 | none | 171 ± 8.7 | 153 ± 10.4 |
| | G (3) | 0 ± 0 | 0 ± 0 |
| | F (4) | 160 ± 4.7 | 138 ± 6.8 |
| | G + F | 0 ± 0 | 0 ± 0 |
| 3T3-CD | none | 131 ± 4/6 | 130 ± 1.7 |
| | G | 123 ± 3.5 | 100 ± 6.8 |
| | F | 14 ± 1.4* | 17 ± 1.4* |
| | G + F | 0 ± 0* | 0 ± 0* |
| PA317 | none | 84 ± 8.1 | 33 ± 2.3 |
| | G | 0 ± 0 | 0 ± 0 |
| | F | 80 ± 2.5 | 40 ± 1.3 |
| | G + F | 0 ± 0 | 0 ± 0 |
| PA-CD-A | none | 187 ± 5.8 | 137 ± 0.9 |
| | G | 123 ± 7.7 | 77 ± 1.2 |
| | F | 3 ± 1.4* | 5 ± 1.5* |
| | G + F | 0 ± 0* | 0 ± 0* |
| PA-CD-B | none | 161 ± 6.0 | 80 ± 2.9 |
| | G | 112 ± 7.9 | 38 ± 3.9 |
| | F | 11 ± 1.7* | 15 ± 1.2* |
| | G + F | 0 ± 0* | 0 ± 0* |
| 3T3-CD-V1 | none | 143 ± 1.5 | |
| | G | 127 ± 4.9 | |
| | F | 9 ± 0.3* | |
| | G + F | 1 ± 0.3* | |
| 3T3-CD-V2 | none | 154 ± 5.2 | |
| | G | 135 ± 4.9 | |

TABLE 2-continued

Relative cloning efficiency in G418 and/or 5FC of cell lines containing the cytosine deaminase gene.

| Cell (1) line | Medium additive | Ave. colony number (sem) | |
|---|---|---|---|
| | | Exp. 1 | Exp. 2 |
| | F | 4 ± 1.2* | |
| | G + F | 3 ± 0.7* | |

(1) Triplicates of each conditions were performed in each experiment.
(2) G is G418 1 mg/ml.
(3) F is 5FC at 0.5 mg/ml.
*P < 0.01 in comparison of (G + F) vs. (G), or (F) vs (—).

5FC also inhibited in vitro proliferation as measured by 3H-thymidine incorporation assays. Table 3 demonstrates nearly complete inhibition of 3H-thymidine incorporation by 5FC in lines 3T3-CD and PA-CD-A at a concentration of 0.5 mg/ml without corresponding effects in the control lines 3T3 and PA317.

TABLE 3

Inhibition of $^3$H-thymidine uptake by 5FC in lines expressing the cytosine deaminase gene.

| Cell | Medium(1) | Ave. cpm + sem(2) | % medium alone(3) |
|---|---|---|---|
| 3T3 | — | 35177 ± 1665 | — |
| | G | 120 ± 14 | 0.3 |
| | F | 50160 ± 1697 | 142 |
| | G + F | 92 ± 13 | 0.3 |
| | 5FU | 880 ± 95* | 2.5 |
| 3T3-CD | — | 15520 ± 1857 | — |
| | G | 15283 ± 2466 | 98.5 |
| | F | 4425 ± 1182* | 28.5 |
| | G + F | 1220 ± 409* | 7.9 |
| | 5FU | 361 ± 33* | 2.3 |
| PA317 | — | 28779 ± 1560 | — |
| | G | 175 ± 23 | 0.6 |
| | F | 21287 ± 1456* | 74.0 |
| | G + F | 120 ± 14* | 0.4 |
| | 5FU | 493 ± 51* | 1.7 |
| PA-CD-A | — | 34813 ± 2791 | — |
| | G | 12416 ± 693 | 35.7 |
| | F | 250 ± 14* | 0.7 |
| | G + F | 178 ± 19* | 0.5 |
| | 5FU | 263 ± 25* | 0.8 |

(1) medium was D10 alone (—), or with G418 1 mg/ml(G), 5FC 0.5 mg/ml(F), or both G418 and 5FC (G + F).
(2) Wells were pulsed at 72 hours with radiolabelled thymidine and harvested 4 hours later. Values represent 12 replicates.
(3) % medium alone = (cpm with medium additive)/(cpm control medium).
*P < 0.01 in comparison of (G + F) vs. (G), (F) vs. (—), or (5FU) vs. (—).

Table 4 summarizes the dose response relationship between 5FC concentration and inhibition of cell line PA-CD-A in both clonogenic and proliferation assays. In line PA-CD-A, 5FC profoundly inhibited both $^3$H-thymidine incorporation and colony counts over a concentration range of 62–500 μg/ml; below that range the effects were diminished somewhat but still significant. No corresponding inhibition of the control PA317 cells were observed.

TABLE 4

5FC selectively eliminates cells expressing the cytosine deaminase gene from mixed population in vitro.

| Cells(1) | Medium(2) | Average colony count ± sem(3) | |
|---|---|---|---|
| | | Exp. 1 | Exp. 2 |
| PA-CD-A | — | 122 ± 5.6 | 126 ± 1.5 |
| | G | 90 ± 4.5 | 85 ± 2.3 |
| | F | 7 ± 0.6 | 14 ± 3.0 |
| | G + F | 0.7 ± 0.3 | 1 ± 0.0 |
| PA317 | — | 83 ± 2.0 | 74 ± 1.5 |
| | G | 0 ± 0 | 0 ± 0 |
| | F | 85 ± 3.0 | 71 ± 5.7 |
| | G + F | 0 ± 0 | 0 ± 0 |
| PA-CD-A + PA317 | — | 164 ± 5.5 | 140 ± 5.6 |
| | G | 83 ± 2.7 | 72 ± 3.2 |
| | F | 84 ± 1.5 | 72 ± 1.5 |
| | G + F | 0.7 ± 0.3 | 1 ± 0.3 |

(1) $10^3$ PA-CD-A, $10^3$ PA317, or $10^3$ PA-CD-A plus $10^3$ PA317 cells were inoculated into wells.
(2) Medium was D10 with the following additives: (—) none, (G) G418 1 mg/ml, (F) 5FC 125 μg/ml, (G + F) G418 1 mg/ml and 5FC 125 μg/ml.
(3) Values represent average and sem of 3 replicates.

Table 5 demonstrates the selectivity of 5FC toxicity in mixed cell populations. Equal numbers of PA-CD-A cells (which contain the cytosine deaminase gene) and PA317 cells (which do not) were mixed and inoculated into wells in clonogenic assays and subjected to selection in 5FC, G418 or both. If the 5FC toxicity were restricted to cells containing the cytosine deaminase gene, one would expect approximately one-half the cells to be eliminated from the mixed population, while nearly all the cells in a pure PA-CD-A population and none of the cells in a pure PA317 population would be affected by 5FC. However if there were significant "bystander killing" by release of cytosine deaminase and/or 5-FU into the medium one would expect both PA-CD-A and PA317 cells in the mixed population to be killed. The colony count in 5FC was approximately one-half the colony count of the mixed population in nonselective media, while control PA317 cells were unaffected by 5FC and PA-CD-A cells were killed.

Finally, the presence and expression of the cytosine deaminase gene had no deleterious effects on cells in the absence of 5FC as judged by cloning efficiency, proliferation in vitro, growth rates in culture or microscopic morphology.

TABLE 5

5FC selectively eliminates cells expressing the cytosine deaminase gene from mixed populations in vitro.

| Cells(1) | Medium(2) | Average colony count ± sem(3) | |
|---|---|---|---|
| | | Exp. 1 | Exp. 2 |
| PA-CD-A | — | 122 ± 5.6 | 126 ± 1.5 |
| | G | 90 ± 4.5 | 85 ± 2.3 |
| | F | 7 ± 0.6 | 14 ± 3.0 |
| | G + F | 0.7 ± 0.3 | 1 ± 0.0 |
| PA317 | — | 83 ± 2.0 | 74 ± 1.5 |
| | G | 0 ± 0 | 0 ± 0 |
| | F | 85 ± 3.0 | 71 ± 5.7 |
| | G + F | 0 ± 0 | 0 ± 0 |
| PA-CD-A | — | 164 ± 5.5 | 140 ± 5.6 |
| | G | 83 ± 2.7 | 72 ± 3.2 |
| | F | 84 ± 1.5* | 72 ± 1.5* |
| | G + F | 0.7 ± 0.3 | 1 ± 0.3 |

(1) $10^3$ PA-CD-A, $10^3$ PA317, or $10^3$ PA-CD-A plus $10^3$ PA317 cells were inoculated into wells.
(2) Medium was D10 with the following additives: (—) none, (G) G418 1 mg/ml, (F) 5FC 125 μg/ml, (G + F) G418 1 mg/ml and 5FC 125 μl/ml.
(3) Values represent average and sem of 3 replicates.
*Values do not differ significantly from PA317 colony counts in unmodified medium or medium containing 5FC.

EXAMPLE 4

Retrovirus Mediated Gene Transfer Results in Successful Expression of the Cytosine Deaminase Gene 3T3 cells were transduced by exposure to the supernatant from cell lines PA-CD-A and PA-CD-B and selected in G418 as described above in the materials and methods section. The resultant cell lines were designated 3T3-CD-V1 (transduced with retrovirus from PA-CD-B) and 3T3-CD-V2 (transduced with retrovirus from PA-CD-A). As seen in Table 1 lysates of both 3T3-CD-V1 and 3T3-CD-V2 converted cytosine to uracil in vitro. They were also sensitive to 5FC in clonogenic assays (Table 2).

While the foregoing invention has been described in some detail for purposes of clarity and understanding, it will be clear to one skilled in the art from a reading of this disclosure that various changes in form and detail can be made without departing from the true scope of the invention.

What is claimed is:

1. A DNA construct that comprises an *E. coli* cytosine deaminase gene linked to a mammalian expression vector, said cytosine deaminase gene modified at the GTG translation initiation codon to ATG to facilitate initiation of translation in a mammalian cell.

2. The DNA construct according to claim 1, wherein the cytosine deaminase gene is obtained from *E. coli*.

3. The DNA construct designated pCD2 which has the accession ATCC #40999.

4. A mammalian host cell comprising said DNA construct according to claim 1, 2 or 3.

5. The mammalian host cell of claim 4 that expresses cytosine deaminase protein.

6. A double negative selection vector comprising an *E. coli* cytosine deaminase gene, a herpes thymidine kinase gene linked to a mammalian expression vector, said cytosine deaminase gene modified at the GTG translation initiation codon to ATG to facilitate initiation of translation in a mammalian cell.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 109 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:1:

```
GAATTCGTTA  ACGCGGTATT  AGGTGGCGCG  CTGAGCTATC  TGATCCTTAA  CCCGATTTTG        60
AATCGTAAAA  CGACAGCAGC  AATGTCGCAT  GTGGAGGCTA  ACAGTGTCG                    109
```

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:2:

```
GAATTCAGGC  TAGCAATGTC  G                                                    21
```

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

```
TGACGCGAAT  TCAGGCTAGC  AATGTCG                                              27
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

```
CACACATTCC  ACAGCGGATC  C                                                    21
```

( 2 ) INFORMATION FOR SEQ ID NO:5:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:5:

CAATGTCGCA TGTGGAGGCT AACAGTGTCG                                                             30